(12) United States Patent
Chou et al.

(10) Patent No.: US 7,329,493 B2
(45) Date of Patent: Feb. 12, 2008

(54) **ONE-TUBE NESTED PCR FOR DETECTING *MYCOBACTERIUM TUBERCULOSIS***

(75) Inventors: George Chin-Sheng Chou, Hsin-Shi (TW); Kai-Pin Huang, Hsin-Shi (TW)

(73) Assignee: AsiaGEN Corporation, Tainan Hsien (TW)

( * ) Notice: Subject to any disclaimer, the term of this patent is extended or adjusted under 35 U.S.C. 154(b) by 255 days.

(21) Appl. No.: 11/017,816

(22) Filed: Dec. 22, 2004

(65) Prior Publication Data

US 2006/0134648 A1    Jun. 22, 2006

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/22.1; 536/24.33; 536/25.32

(58) Field of Classification Search ............ 435/6, 435/91.2; 536/22.1, 24.33, 25.32
See application file for complete search history.

(56) References Cited

U.S. PATENT DOCUMENTS 5,731,150 A * 3/1998 Sandhu et al. ............... 435/6
6,224,881 B1 * 5/2001 Riley et al. ............... 424/248.1

OTHER PUBLICATIONS

Yuen et al., Kwok-Yung; Comparison of Two Automated DNA Amplification Systems with a Manual One-Tube Nested PCR Assay for Diagnosis of Pulmonary Tuberculosis; Journal of Clinical Microbiology; Jun. 1997, p. 1385-1389.
Nucleotide Y14047. Reports *Mycobacterium tub.* . . [gi:2239147]; Dec. 8, 2004.

* cited by examiner

*Primary Examiner*—Kenneth R. Horlick
*Assistant Examiner*—Joyce Tung
(74) *Attorney, Agent, or Firm*—Troxell Law Office, PLLC

(57) ABSTRACT

The present invention relates to a kit and method for detecting *M. tuberculosis* of suspected patient. The present invention also relates to primers and probe used to detect *M. tuberculosis* by performing one tube nested PCR.

17 Claims, 8 Drawing Sheets

001 GCGTAGGCGT CGGTCACAAA GGCCACGTAG GCGAACCCTG

041 CCCAGGTCGA CACATAGGTG AGGTCTGCTA CCCACAGCCG

081 GTTAGGTGCT GGTGGTCCGA AGCGGCGCTG GACGAGATCG

121 GCGGGACGGG CTGTGGCCGG ATCAGCGATC GTGGTCCTGC

161 GGGCTTTGCC GCGGGTGGTC CCGGACAGGC CGAGTTTGGT

201 CATCAGCCGT TCGACGGTGC ATCTGGCCAC CTCGATGCCC

241 TCACG

2). Sequences of primers and probe:

_AG 005_                          AG 007

001 GGCCGCGGGA ATTCGATTGC GTAGGCGTCG GTCACAAAGG

AG 007

041 CCACGTAGGC GAACCCTGCC CAGGTCGACA CATAGGTGAG

OTNP 001                    OTNP 003
               2031

081 GTCTGCTACC CACAGCCGGT TAGGTGCTGG TGGTCCGAAG

OTNP 003

121 CGGCGCTGGA CGAGATCGGC GGGACGGGCT GTGGCCGGAT

161 CAGCGATCGT GGTCCTGCGG GCTTTGCCGC GGGTGGTCCC

AG 006

201 GGACAGGCCG AGTTTGGTCA TCAGCCGTTC GACGGTGCAT

OTNP 004        OTNP 002
AG 006
                    AG 004
241 CTGGCCACCT CGATGCCCTC ACGAATCACT AGTGAATTCG
                OTNP 002

Figure 1 (continued)

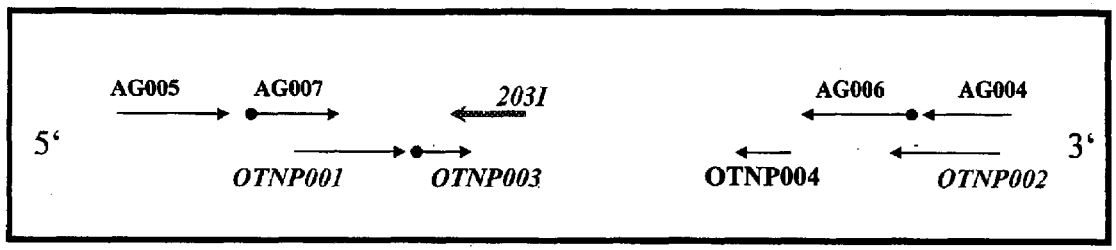

(c)

Primer set I: Outer primer pairs

No. 2 (OTNP 001): 5'-CACGTAGGCG AACCCTGCCC AGGTC-3'

25mer   Tm=66~76°C

No. 3 (AG005): 5'-GCGTAGGCGT CGGTCACAAA-3'

20mer   Tm: 64°C

No. 4 (OTNP 002): 5'-GTGAGGGCAT CGAGGTGGCC AGATG-3'

25mer   Tm=64~76°C

No. 5 (AG004): 5'-CGTGAGGGCA TCGAGGTGGC-3'

20mer   Tm: 68°C

Primer set II: Inner primer pairs

No. 6 (OTNP 003): Biotin-5'-GACACATAGG TGAGGTCTGC-3'

20mer   Tm=46~55°C

No. 7 (AG007): Biotin-5'-GCCACGTAGG CGAACCCTG-3'

19mer   Tm: 64°C

No. 8 (OTNP 004): 5'-ACGGCTGA TGACCAAACT-3'

18mer   Tm=47~56°C

No. 9 (AG006): Biotin-5'-AGATGCACCG TCGAACGG-3'

18mer   Tm: 58°C

Figure 1 (continued)

No. 10(Probe 2031 sequence):

TTTTTTTTTTACCTAACCGGCTGTGGGTAGCAGA

34mer (a)

| Method | Positive Result | Negative Result |
|---|---|---|
| Two-tube nested PCR* | 29 | 71 |
| One-tube nested PCR | 34 | 66 |
| Gold Standard** | 31 | 69 |

SEQUENCE LISTING

<160> NUMBER OF SEQ ID NOS: 11

<210> SEQ ID NO 1
<211> LENGTH: 245
<212> TYPE: DNA
<213> ORGANISM: Mycobacterium tuberculosis

<400> SEQUENCE: 1

```
gcgtaggcgt cggtcacaaa ggccacgtag gcgaaccctg cccaggtcga cacataggtg      60
aggtctgcta cccacagccg gttaggtgct ggtggtccga agcggcgctg gacgagatcg     120
gcgggacggg ctgtggccgg atcagcgatc gtggtcctgc gggctttgcc gcgggtggtc     180
```

```
ccggacaggc cgagtttggt catcagccgt tcgacggtgc atctggccac ctcgatgccc    240
tcacg                                                                245

<210> SEQ ID NO 2
<211> LENGTH: 25
<212> TYPE: DNA
<213> ORGANISM: Mycobacterium tuberculosis

<400> SEQUENCE: 2
cacgtaggcg aaccctgccc aggtc                                          25

<210> SEQ ID NO 3
<211> LENGTH: 20
<212> TYPE: DNA
<213> ORGANISM: Mycobacterium tuberculosis

<400> SEQUENCE: 3
gcgtaggcgt cggtcacaaa                                                20

<210> SEQ ID NO 4
<211> LENGTH: 25
<212> TYPE: DNA
<213> ORGANISM: Mycobacterium tuberculosis

<400> SEQUENCE: 4
gtgagggcat cgaggtggcc agatg                                          25

<210> SEQ ID NO 5
<211> LENGTH: 20
<212> TYPE: DNA
<213> ORGANISM: Mycobacterium tuberculosis

<400> SEQUENCE: 5
cgtgagggca tcgaggtggc                                                20

<210> SEQ ID NO 6
<211> LENGTH: 20
<212> TYPE: DNA
<213> ORGANISM: Mycobacterium tuberculosis

<400> SEQUENCE: 6
gacacatagg tgaggtctgc                                                20

<210> SEQ ID NO 7
<211> LENGTH: 19
<212> TYPE: DNA
<213> ORGANISM: Mycobacterium tuberculosis

<400> SEQUENCE: 7
gccacgtagg cgaaccctg                                                 19

<210> SEQ ID NO 8
<211> LENGTH: 18
<212> TYPE: DNA
<213> ORGANISM: Mycobacterium tuberculosis

<400> SEQUENCE: 8
acggctgatg accaaact                                                  18

<210> SEQ ID NO 9
<211> LENGTH: 18
<212> TYPE: DNA
<213> ORGANISM: Mycobacterium tuberculosis
```

```
<400> SEQUENCE: 9
agatgcaccg tcgaacgg                                                      18

<210> SEQ ID NO 10
<211> LENGTH: 34
<212> TYPE: DNA
<213> ORGANISM: Mycobacterium tuberculosis

<400> SEQUENCE: 10
tttttttttt acctaaccgg ctgtgggtag caga                                    34

<210> SEQ ID NO 11
<211> LENGTH: 280
<212> TYPE: DNA
<213> ORGANISM: Mycobacterium tuberculosis

<400> SEQUENCE: 11
ggccgcggga attcgattgc gtaggcgtcg gtcacaaagg ccacgtaggc gaaccctgcc        60
caggtcgaca cataggtgag gtctgctacc cacagccggt taggtgctgg tggtccgaag       120
cggcgctgga cgagatcggc gggacgggct gtggccggat cagcgatcgt ggtcctgcgg       180
gctttgccgc gggtggtccc ggacaggccg agtttggtca tcagccgttc gacggtgcat       240
ctggccacct cgatgccctc acgaatcact agtgaattcg                             280
```

ONE-TUBE NESTED PCR FOR DETECTING *MYCOBACTERIUM TUBERCULOSIS*

FIELD OF THE INVENTION

The present invention relates to a kit and a method for detecting *Mycobacterium tuberculosis* (*M. tuberculosis*) in a sample by the use of a nested polymerase chain reaction (PCR). The present invention also relates to primers and probe for detecting the presence of *M. tuberculosis*.

BACKGROUND OF THE INVENTION

Tuberculosis (TB) is the leading infectious killer of youth and adults and the first most common infectious disease worldwide. One third of the world's population is currently infected and 20 million of those infected are active cases. TB will kill 30 million people this decade. More than 50 million people may already be infected with multidrug-resistant (MDR) strains of TB. TB is now becoming the leading cause of death among HIV positive people where it kills much more rapidly with a fatality of 80%.

Tuberculosis is caused by infection with *M. tuberculosis*, a bacillus bacterium. It is spread by aerosol droplets and causes irreversible lung destruction. If it escapes the lung it may cause systemic disease affecting many organs including bones, joints, liver, spleen, gastrointestinal tract and brain. 50% of people exposed to *M. tuberculosis* are infected with the bacteria and 15% of those infected develop disease. Poverty, malnutrition and overpopulation contribute dramatically to the perseverance and wild spread of tuberculosis.

Past means of controlling TB have involved the use of combinations of antibiotics. Recently, because of complications due to MDR strains, the number and combination of antibiotics administered must be individually tailored depending on the strain the patient is harboring. In extreme cases, surgical removal of the infected portion of the lung is required.

Traditionally, the diagnosis of TB has been made on the basis of clinical findings and chest radiographs and confirmed by sputum or tissue smears that show TB bacilli. These methods remain the "gold standard" for diagnosis, but development of DNA probes, polymerase chain reaction (PCR) assays, and liquid media now allow more sensitive and rapid diagnosis. Unfortunately, increased sensitivity of rapid techniques is not always associated with increased specificity.

The Amplified *M. tuberculosis* Direct Test (Gen-Probe) targets mycobacterial ribosomal RNA by transcription-mediated amplification. The test uses DNA probes that are highly specific for *M. tuberculosis* species. It is best used (and only approved for use) in patients in whom acid-fast bacilli smears are positive and cultures are in process. Since specificity is less than 100%, even in patients with positive smears, occasional false-positive results do occur, usually in patients with nontuberculous mycobacterial infections.

W. C. Yam et al, published "DIRECT DETECTION OF MYCOBACTERIUM TUBERCULOSIS IN CLINICAL SPECIMENS USING SINGLE-TUBE BIONTINYLATED NESTED POLYMERASE CHAIN REACTION-ENZYME LINKED IMMUNOASSAY (PCR-ELISA)" in Diagnostic Microbiology and Infection Disease, 48 (2004) p. 271-275, provided an improved assay for detecting *M. tuberculosis*. However, it takes around 2 hours for performing hot start to activate Taq polymerase and the amplification for the outer and inner PCR products.

The trend of diagnostic laboraory medicine is automation, and nucleic acid amplification assays are no exception to this rule. The known method (such as real-time PCR assay) using the LightCycler (LC) instrument provides a rapid, sensitive and specific means to identify *M. tuberculosis*. However, the use of LC as a routine diagnosis of *M. tuberculosis* remains limited at present. It is because the installment and maintenance cost may not be afforded by most of the center.

It still has a method, system and kit to provide a simple, low-cost, accurate, high throughput and saving-labor and operation time to detect DNA of *M. tuberculosis* in a sample with comparable sensitivity and specificity with commercial products.

SUMMARY OF THE INVENTION

The present invention provides a kit for detecting the presence or absence of *Mycobacterium tuberculosis* in a sample using a nested polymerase chain reaction, comprising (i) an outer pair of oligonucleotide primers selected from the group consisting of (a) SEQ ID NOS: 2 and 4, and (b) SEQ ID NOS: 3 and 5, and (ii) an inner pair of oligonucleotide primers selected from the group consisting of (c) SEQ ID NOS: 6 and 8, and (d) SEQ ID NOS: 7 and 9, wherein the concentration of the outer pair of oligonucleotide primers to the concentration of the inner pair of oligonucleotide primers is 1:5 to 1:100.

The present invention further provides a method for detecting the presence or absence of *Mycobacterium tuberculosis* in a sample using a nested polymerase chain reaction, comprising (i) adding into one tube with DNA from the sample, buffer, dNTP, Taq polymerase, probe having SEQ ID NO: 10, an outer pair of oligonucleotide primers selected from the group consisting of (a) SEQ ID NOS: 2 and 4, and (b) SEQ ID NOS: 3 and 5, and an inner pair of oligonucleotide primers selected from the group consisting of (c) SEQ ID NOS: 6 and 8, and (d) SEQ ID NOS: 7 and 9 to form a mixture, wherein the concentration of the outer pair of oligonucleotide primers to the concentration of the inner pair of oligonucleotide primers is 1:5 o 1:100;

(ii) performing first 20-50 cycles of amplification for PCR products from the outer primers;

(iii) performing following 10-30 cycles of amplification PCR products from for the inner primers; and (iv) identifying *M. tuberculosis* by the probe.

The present invention also provides novel nucleotide sequences for detecting the presence or absence of *M. tuberculosis*.

BRIEF DESCRIPTION OF THE DRAWINGS

FIG. 1 (*a*). IS6110 sequence (SEQ ID NO. 1) and the position of SEQ ID NOS. 2-9: (*b*). sequences of primers and probe (collectively. SEQ ID NO: 11): and (*c*) outer and inner primer pairs and probe.

Figure 3:
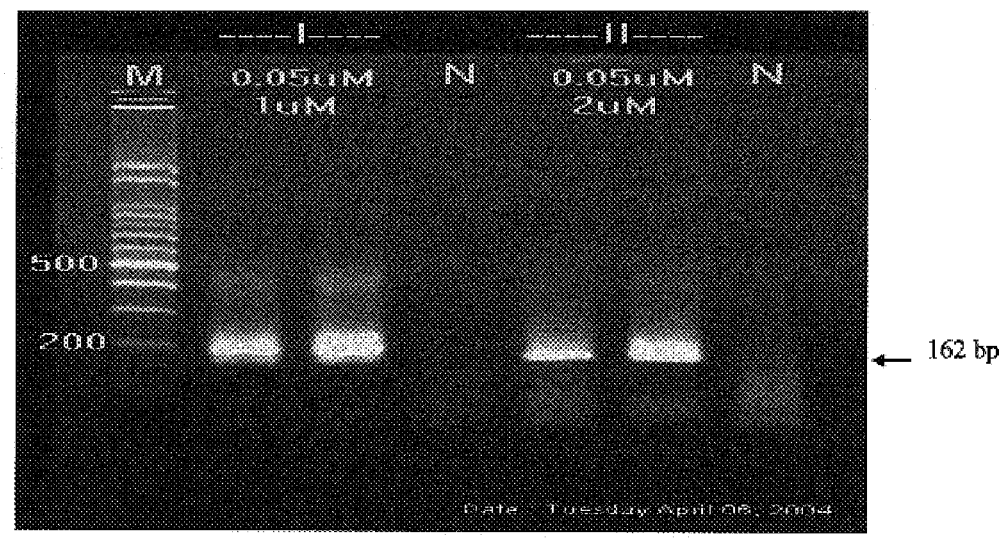

FIG. 3 shows the proper concentration of primers for both outer primers and inner primers. In the figure, 0.05 µM for Outer primer SEQ ID NOS:2 and 4; and 1 µM and 2 µM for Inner primer SEQ ID NOS:6 and 8. "162 bp" means the PCR product amplified from one tube two-phase PCR using as the target for proof-reading by specific probe.

Figure 4:
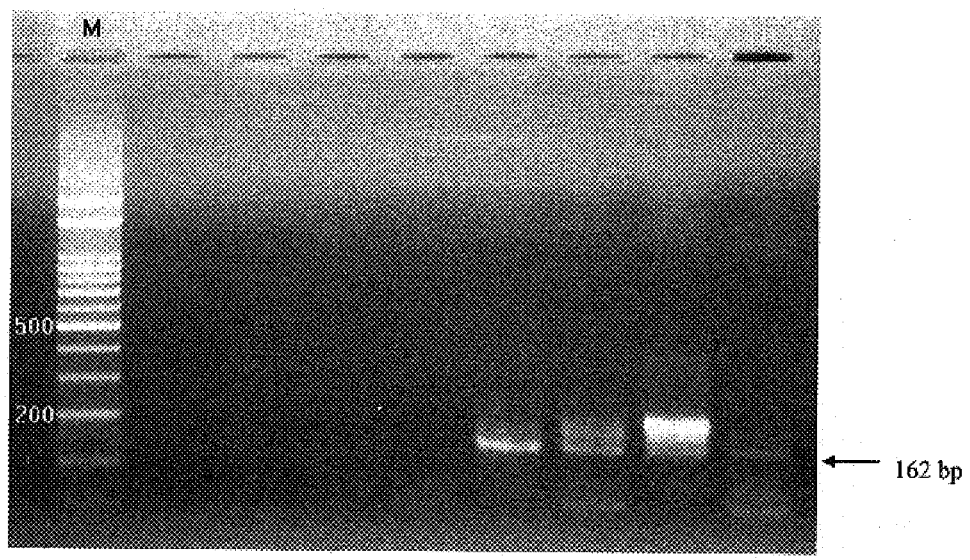

FIG. 4 shows clinical MTB samples detected by MTB one tube nested-PCR assay. In this figure, NC means negative control; NTM means non-tuberculosis mycobacterium; MAC: mycobacterium avium; PC denotes positive control and TB means *mycobacterium tuberculosis* clinical samples.

Figure 5:
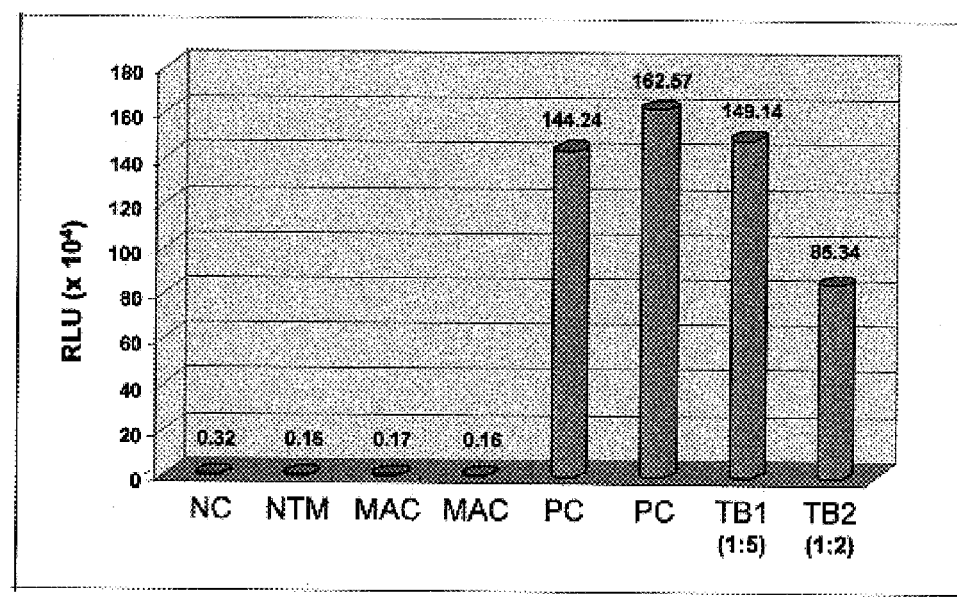

FIG. 5 shows clinical MTB samples detected by one tube nested-PCR-based MTB assay of the invention. In this figure, NC means negative control; NTM means non-tuberculosis *mycobacterium*; MAC: *mycobacterium* avium; PC denotes positive control; TB means *mycobacterium tuberculosis* clinical samples; TB1 denotes *mycobacterium tuberculosis* from patient 1 and TB1 denotes *Mycobacterium tuberculosis* from patient 2.

FIG. 6 shows the comparison of the result of one tube nested PCR, two tubes nested PCR and the gold standard (culture confirmation). In this figure, ** Gold Standard means medium culture method.

DETAILED DESCRIPTION OF THE INVENTION

Target Gene

The present invention is related to nucleotide sequences comprising highly specific oligonucleotide primers that are synthesized from and hybridize to specific portions of a 219 base-pair region of the *M. tuberculosis* IS6110 gene having the nucleotide sequence set forth in SEQ ID NO: 1. The nucleotide sequence for this gene has been published (seq ID:gi:2239147). The 219 base-pair region set forth in SEQ ID NO: 1 represents nucleotides 2385-2604 of the published *M. tuberculosis* IS6110 gene sequence (GenBank Accession No. Y14047).

Primers for use in the invention are selected from a 219 base-pair region of the *M. tuberculosis* IS6110 gene (see SEQ ID NO: 1). The nucleotide sequences for preferred primers of the present invention are set forth in SEQ ID NOS: 2-9. In addition, the present invention also provides a novel probe having SEQ ID NO: 10 for identifying the nested PCR products.

Therefore, the present invention provides a nucleotide sequence for detecting the presence or absence of *M. tuberculosis* is selected from the group consisting of

| | |
|---|---|
| 5'-CACGTAGGCG AACCCTGCCC AGGTC-3' | SEQ ID NO: 2 |
| 5'-GCGTAGGCGT CGGTCACAAA-3' | SEQ ID NO: 3 |
| 5'-GTGAGGGCAT CGAGGTGGCC AGATG-3' | SEQ ID NO: 4 |
| 5'-CGTGAGGGCA TCGAGGTGGC-3' | SEQ ID NO: 5 |
| 5'-GACACATAGG TGAGGTCTGC-3' | SEQ ID NO: 6 |
| 5'-GCCACGTAGG CGAACCCTG-3' | SEQ ID NO: 7 |
| 5'-ACGGCTGA TGACCAAACT-3' | SEQ ID NO: 8 |

-continued

| | |
|---|---|
| 5'-AGATGCACCG TCGAACGG-3' | SEQ ID NO: 9 |
| TTTTTTTTTTACCTAACCGGCTGTGGGTAGCAGA | SEQ ID NO: 10. |

The preferred embodiment of the nucleotide sequence of the invention is selected from the group consisting of SEQ ID NO:2, SEQ ID NO:4, SEQ ID NO:6 and SEQ ID NO:8.

These single-stranded primers are comprised of nucleotide sequences including naturally occurring nucleotides and any variants thereof. By "naturally occurring nucleotides" is intended adenosine triphosphate, guanosine triphosphate, cytosine triphosphate, thymidine triphosphate, uridine triphosphate, and inosine triphosphate. By "any variants thereof" is intended any nucleotides comprising modified bases of the form N6-(6-aminohexyl) (as in N6-(6-aminohexyl) dATP or N6-(6-aminohexyl) ATP), or comprising bases modified as 5'-thiol, 5'-phospho, 5'-methyl, 5'-biotinylated, 5'-amino, or 5'-fluoro (as in 5'-fluoro-deoxyadenosine).

These primers are designed for desirable characteristics, including inability to form hairpin loops. Additionally, when any two of these primers are used as a primer pair for a polymerase chain reaction method according to the present invention, they do not hybridize to each other. All of these characteristics enable a highly sensitive, highly specific nested polymerase chain reaction approach for detection of the *M. tuberculosis* in potentially infected samples.

Primers for Nested PCR

In an embodiment of the present invention, these primers are used in a nested polymerase chain reaction (PCR) method to detect the presence of the 219 base-pair region of the *M. tuberculosis* IS6110 gene in a purified sample nucleic acid mixture, the nucleotide sequences of which have been extracted from a potentially infected sample. By "nested" PCR method is intended a two-staged polymerase chain reaction process. In a first-stage polymerase chain reaction, a pair of "outer" oligonucleotide primers, consisting of an upper and a lower primer that flank a particular first "target" nucleotide sequence in the 5' and 3' position, respectively, are used to amplify that first sequence. In a second-stage polymerase chain reaction, a second set of "inner" or "nested" oligonucleotide primers, also consisting of an upper and a lower primer, is used to amplify a smaller second "target" nucleotide sequence that is contained within the first target nucleotide sequence.

The upper and lower inner primers flank the second target nucleotide sequence in the 5' and 3' positions, respectively. By "flanking primers" is intended primers that are complementary to segments on the 3'-end portions of the double-stranded target nucleotide sequence that is amplified during the PCR process. By "target" nucleotide sequence is intended a nucleotide sequence comprising a predetermined portion of the 219 base-pair region of the *M. tuberculosis* IS6110 gene set forth in SEQ ID NO: 1. The base-pair size of these target nucleotide sequences and their particular position within the 219 base-pair region of the gene are determined by the pair of outer primers and pair of inner primers used in the first- and second-stage polymerase chain reactions, respectively.

PCR and Nested PCR References

Nested PCR methods are available in the art. See generally U.S. Pat. No. 4,683,202, U.S. Pat. No. 5,487,969 (herpes B virus); U.S. Pat. No. 5,545,523 (bovine herpes virus-1); more particularly for the *M. tuberculosis*, see Yuen K Y, et al., *J Clin Microbiol.* 1997 35(6):1385-9.; Yam W C, et al. *Diagn Microbiol Infect Dis.* 2004 48(4):271-5.

Samples of *M. tuberculosis*

The primers and nested PCR method of the present invention can be utilized for the detection of the presence or absence of the *M. tuberculosis* in any sample nucleic acid mixture isolated from any tissue sample suspected of harboring the *M. tuberculosis*. By "sample nucleic acid mixture" is intended a sample containing nucleic acids and mixtures thereof from any individual, strain, species, or genera of organism.

Procedures of Nested PCR—Isolate DNA

The nested PCR method of the present invention comprises the following steps. A sample nucleic acid mixture is first isolated from a tissue sample suspected of being infected with the *M. tuberculosis* and then purified by centrifugation. Methods for isolation and preparation of the purified *M. tuberculosis* nucleic acid mixture are available in the art. See, for example, Yuen K Y, et al., *J Clin Microbiol.* 1997 35(6):1385-9.; Yam W C, et al. *Diagn Microbiol Infect Dis.* 2004 48(4):271-5.

Procedures of One Tube Nested PCR—First Stage

The nested PCR method of the present invention comprises the following steps. In a first-stage polymerase chain reaction, specific outer oligonucleotide primers are added to the sample nucleic acid mixture, and the resulting mixture is subjected to an initial denaturation step to obtain single-stranded DNA templates. Following denaturation, the mixture is subjected to an initial annealing step, where the outer primers hybridize to opposite strands of the first targeted nucleotide sequence. The temperature is then raised to allow for extension or replication of the specific segment of DNA across the region between the two primers by a thermostable DNA polymerase. The reaction is then thermocycled to allow for repeated denaturation, annealing, and extension, so that at each cycle, the amount of DNA representing the targeted nucleotide sequence between the two outer primers is doubled and the specific amplification of a first selected portion of the 219 base-pair region of the IS6110 gene is amplified.

The first nucleotide sequence within the 219 base-pair region of the IS6110 gene, which is targeted for amplification in the first-stage polymerase chain reaction, is flanked by an upper primer in the 5' upstream position and a lower primer in the 3' downstream position. The first targeted nucleotide sequence, and hence the amplification product of the first-stage polymerase chain reaction, has a predicted base-pair length, which is determined by the base-pair distance between the 5' upstream and 3' downstream hybridization positions of the upper and lower primers, respectively, of the outer primer pair. The upper and lower primers of the outer primer pair are derived from the 219 base-pair region of the *M. tuberculosis* IS6110 gene (see SEQ ID NO: 1). For purposes of the present invention, the upper primer of the outer primer pair is preferably selected from the nucleotide sequences set forth in SEQ ID NOS:2 and 3, and more preferably is the nucleotide sequence set forth in SEQ ID NO:2 The lower primer of the outer primer pair is preferably selected from the nucleotide sequences set forth in SEQ ID NOS:4 and 5, and more preferably is the nucleotide sequence set forth in SEQ ID NO:4.

Procedures of One Tube Nested PCR—Second Stage

In this second-stage reaction, the products of the first-stage reaction are combined with specific inner or nested primers. These inner primers are derived from nucleotide sequences within the first targeted nucleotide sequence and flank a second, smaller targeted nucleotide sequence contained within the first targeted nucleotide sequence. This mixture is subjected to initial denaturation, annealing, and extension steps, followed by thermocycling as before to allow for repeated denaturation, annealing, and extension or replication of the second targeted nucleotide sequence. This second targeted nucleotide sequence is flanked by an upper primer in the 5' upstream position and a lower primer in the 3' downstream position. The second targeted nucleotide sequence, and hence the amplification product of the second-stage PCR, also has a predicted base-pair length, which is determined by the base-pair distance between the 5' upstream and 3' downstream hybridization positions of the upper and lower primers, respectively, of the inner primer pair. The upper and lower primers of the inner primer pair are derived from within the 219 base-pair region of the *M. tuberculosis* IS6110 gene (see SEQ ID NO: 1). For purposes of the present invention, the upper primer of the inner primer pair is preferably selected from the nucleotide sequences set forth in SEQ ID NOS: 6 and 7, and more preferably is the nucleotide sequence set forth in SEQ ID NO:6. The lower primer of the inner primer pair is preferably selected from the nucleotide sequences set forth in SEQ ID NOS: 8 and 9, and more preferably is the nucleotide sequence set forth in SEQ ID NO: 8.

Considerations of One Tube Nested PCR

In the present invention, following protocols first disclosed by Erlich, H. A., et al., *Science,* 252, 1643, 1991, a "drop-in, drop-out" nesting in which both primer pairs are present initially and no manipulation of the reaction mixture is needed during the course of amplification is performed to minimize the risk of sample cross-contamination. Generally, the outer primer set is longer, or has a higher GC content than the inner set. In addition, it is implied that the extension product of the outer primer set is substantially longer or has a higher GC content than the inner primer extension product. If sufficiently high annealing and denaturation temperatures are used in the first stage, inner primer annealing is prevented while outer primer annealing, extension and denaturation proceeds. The annealing and denaturation temperatures in the second stage are reduced to enable inner primer annealing and to prevent outer primer extension product denaturation. The inner primers are thus "dropped in" in the second stage by proceeding with a reduced annealing temperature, and outer primer amplification is a "dropped out" by the lower denaturation temperature.

In general, the melting temperature, concentrations and annealing times of primers in the first and second stages were optimized and nesting was performed in which both primer pairs are present initially and no manipulation of the reaction mixture is needed during the course of amplification to minimize the risk of sample cross-contamination.

In a preferred embodiment of the present invention, the temperature of annealing and the temperature of extension in the first-stage polymerase chain reaction is at 72° C. The concentration of the outer pair of oligonucleotide primers to inner pair of oligonucleotide primers is 1:10 to 1:50, preferably being 1:20. The cycle of amplification for PCR products from the outer primers is 25-45, preferably being 35. The cycle of amplification for PCR products from the inner primers is 10-30, preferably being 20.

To increase specificity for detecting the presence of *M. tuberculosis*, the present invention further comprises treating the mixture consisting of DNA from sample, buffer, dNTP, Taq polymerase, probe and primers over 5 minutes at 94° C.

Analyze Product of Nested PCR

The amplification products of the first- and second-stage polymerase chain reaction may be analyzed to identify the presence or absence of the first and second targeted nucleotide sequences comprising specific portions of the 219 base-pair region of the IS6110 gene. Identification of the amplification products, as being derived from the *M. tuberculosis* IS6110 gene, may be accomplished by any one of several methods known in the art to detect amplified nucleotide sequences. These methods include, but are not limited to, determination of size, restriction enzyme digestion pattern, subsequent cloning of amplification products, Southern blot hybridization, with an oligonucleotide probe internal to the nucleotide sequence being amplified, or DNA sequencing.

Analyze Product of Nested PCR—Electrophoresis

The size of the product or products may be determined by electrophoresis through a gel, preferably an agarose gel, simultaneously with molecular size standards of known base-pair length. The gel may be stained with ethidium bromide, which intercalates between base pairs and enables the visualization of DNA upon illumination with ultraviolet light. In this manner, amplification products from the first- or second-stage PCR having equidistant migration with molecular size standards of approximately the base-pair length of the predicted first or second targeted nucleotide sequence, respectively, would verify presence of the *M. tuberculosis* IS6110 gene, and hence the *M. tuberculosis*, within the original tissue sample.

Analyze Product of Nested PCR—Restriction Endonuclease Digest

Further verification of product specificity for a region within the *M. tuberculosis* IS6110 gene may be performed by restriction endonuclease digest of the amplification products of the completed first- and second-stage polymerase chain reactions. Following digestion with restriction enzymes specific for known base-pair positions within the first or second targeted nucleotide sequence, the base-pair length of the digestion products may be determined using gel electrophoresis and ethidium bromide staining as described above. Depending upon the base-pair location of the restriction enzyme cut within the first- or second-stage PCR amplified nucleotide sequence, digestion would yield two nucleotide sequence fragments of predicted size. In this manner, digestion products from the first- or second-stage PCR amplified nucleotide sequences having equidistant migration with molecular size standards of approximately the base-pair length of the predicted nucleotide sequence fragments would verify presence of the *M. tuberculosis* IS6110 gene, and hence the bcteria, within the original tissue sample.

Accordingly, the present invention provides a method for detecting the presence or absence of *Mycobacterium tuberculosis* in a sample using a nested polymerase chain reaction, comprising (i) adding into one tube with DNA from sample, buffer, dNTP, Taq polymerase, probe having SEQ ID NO: 10, an outer pair of oligonucleotide primers selected from the group consisting of (a) SEQ ID NOS: 2 and 4, and (b) SEQ ID NOS: 3 and 5, and an inner pair of oligonucleotide primers selected from the group consisting of (c) SEQ ID NOS: 6 and 8, and (d) SEQ ID NOS: 7 and 9 to form a mixture, wherein the concentration of the outer pair of oligonucleotide primers to the concentration of the inner pair of oligonucleotide primers is 1:5 o 1:100;

(ii) performing 20-50 cycles of amplification for PCR products from the outer primers in the first-stage polymerase chain reaction;

(iii) performing following 10-30 cycles of amplification PCR products from for the inner primers in the second-stage polymerase chain reaction; and (iv) identifying *M. tuberculosis* by the probe.

In the present method, the temperature of annealing and the temperature of extension in the first-stage polymerase chain reaction is the same. In the preferred embodiment, the temperature is 72° C.

The concentration of the outer pair of oligonucleotide primers to inner pair of oligonucleotide primers is 1:10 to 1:50, preferably being 1:20. The cycle of amplification for PCR products from the outer primers is 25-45, preferably being 35. The cycle of amplification for PCR products from the inner primers is 10-30, preferably being 20.

To increase specificity for detecting the presence of *M. tuberculosis*, the present invention further comprises treating the mixture consisting of DNA from sample, buffer, dNTP, Taq polymerase, probe and primers over 5 minutes at 94° C.

Analyze Product of Nested PCR—Labeled Primers

In another embodiment, labeled primer pairs in the first or/and second stage of amplification could be used in the nested PCR amplification to detect the amplification product directly. Commonly employed labels include, but are not limited to, fluorescent molecules, radioactive molecules, chromogenic substrates, biotin, acridinium ester and acridinium-9-carboxamide. The methods for biotinylating nucleic acids are well known in the art, as are methods for introducing fluorescent molecules and radioactive molecules into oligonucleotides and nucleotides. In the preferred embodiment of the invention, the inner pair of oligonucleotide primers is labeled by biotin.

When biotin is employed, it is detected by avidin, streptavidin or the like, which is conjugated to a detectable marker, such as an enzyme (e.g., horseradish peroxidase). Enzyme conjugates are commercially available from, for example, Vector Laboratories (Burlingame, Calif.). Steptavidin binds with high affinity to biotin, unbound streptavidin is washed away, and the presence of horseradish peroxidase enzyme is then detected using a luminescence-emission substrate in the presence of peroxide and appropriate buffers. The product may be detected using a Berthold Luminometer (Pforzheim, Germany).

Detection methods are well known for fluorescent, radioactive, chemiluminescent, chromogenic labels, as well as other commonly used labels. Briefly, chemiluminescence can be identified and quantitated most directly by their emission wavelengths and intensity.

Analyze Product of Nested PCR-Southern Blot

In still another embodiment, a probe may be used to detect the amplification product of the nested PCR. As used herein, a "probe" is a substance, e.g., a molecule, which can be specifically recognized by a particular target. Commonly employed labels include, but are not limited to, biotin, fluorescent molecules, radioactive molecules, chromogenic substrates, chemi-luminescence, and the like. Detection methods are well known for fluorescent, radioactive, chemiluminescent, chromogenic labels, as well as other commonly used labels. In the preferred embodiment of the invention, the probe is SEQ ID No. 10(Probe 2031 sequence): TTTTTTTTTTACCTAACCGGCTGTGGGTAGCAGA.

The preferred method of verifying the amplification product of nested PCR, further disclosed in the example, is by biotinylating one of the primers of inner primer pairs. The biotinylated product of the second amplification stage could be identified using luminometer. Other methods of verifying the amplification product may be used in combinatory to increase the accuracy of detecting *M. tuberculosis* in suspected samples.

Kits of Invention

The present invention also provides a kit for detecting the presence or absence of *Mycobacterium tuberculosis* in a sample using a nested polymerase chain reaction, comprising (i) an outer pair of oligonucleotide primers selected from the group consisting of (a) SEQ ID NOS: 2 and 4, and (b) SEQ ID NOS: 3 and 5, and (ii) an inner pair of oligonucleotide primers selected from the group consisting of (c) SEQ ID NOS: 6 and 8, and (d) SEQ ID NOS: 7 and 9, wherein the concentration of the outer pair of oligonucleotide primers to the concentration of the inner pair of oligonucleotide primers is 1:5 to 1:100.

The kit of the present invention could be applied to know PCR methods (such as one-tube or two-tube nested PCR). In the preferred embodiment, the kit of the present invention is applied to one-tube nested PCR reaction.

In the preferred embodiment, the concentration of the outer pair of oligonucleotide primers to the concentration of the inner pair of oligonucleotide primers is 1:10 to 1:50. In the more preferred embodiment of the kit, the concentration of the outer pair of oligonucleotide primers to the concentration of the inner pair of oligonucleotide primers is 1:20.

The present invention provides for "kits" comprising the elements necessary to detect the presence or absence of the *M. tuberculosis* in a sample using the nested PCR method of the invention. Such a kit may comprise a carrier being compartmentalized to receive in close confinement therein one or more container means, such as tubes or vials. One of said container means may contain at least two nucleotide sequences for an outer pair of oligonucleotide primers for use in a first-stage polymerase chain reaction, and at least two nucleotide sequences for an inner pair of oligonucleotide primers for use in a second-stage polymerase chain reaction. These outer and inner primer pairs, each consisting of a 5' upper primer and a 3' lower primer, are derived from the 219 base-pair region of the *M. tuberculosis* IS6110 gene (SEQ ID NO: 1). For the purposes of the present invention, the upper primer of the outer primer pair is preferably selected from the nucleotide sequences set forth in SEQ ID NOS: 2 and 3; and more preferably has the nucleotide sequence set forth in SEQ ID NO:2. The lower primer of the outer primer pair is preferably selected from the nucleotide sequences set forth in SEQ ID NOS:4 and 5, and more preferably has the nucleotide sequence set forth in SEQ ID NO:4; the upper primer of the inner primer pair is preferably selected from the nucleotide sequences set forth in SEQ ID NOS:6 and 7, and more preferably has the nucleotide sequence set forth in SEQ ID NO:6; and the lower primer of the inner primer pair is preferably selected from the nucleotide sequences set forth in SEQ ID NOS: 8 and 9, and more preferably has the nucleotide sequence set forth in SEQ ID NO: 8. These primers may be present in appropriate storage buffers.

One or more said container means of such a kit may contain one or more enzymes or reagents to be used in the nested PCR method of the invention. These enzymes may be present singly or in a mixture, in the lyophilized state or in an appropriate storage buffer. The kit may also contain any additional materials needed to carry out the detection method of the invention, such as buffers, extraction and purification reagents, nucleic acids, nucleotides (dNTPs), pipettes, plates, filter paper, gel electrophoresis materials, transfer materials, and the like.

The kit of the invention further comprises a probe to detect the amplification product of the nested PCR. In the preferred embodiment of the invention, the probe is SEQ ID No. 10(Probe 2031 sequence): TTTTTTTTTT ACCTMCCGGCTGTGGGTAGCAGA.

The probe can be specifically recognized by a particular target. Commonly employed labels include, but are not limited to, biotin, fluorescent molecules, radioactive molecules, chromogenic substrates, chemi-luminescence, and the like. Detection methods are well known for fluorescent, radioactive, chemiluminescent, chromogenic labels, as well as other commonly used labels.

The following experiments are offered by way of illustration and not by way of limitation.

EXAMPLES

The examples below are non-limiting and are merely representative of various aspects and features of the present invention.

Example 1

Testing the Melting Temperature of Primers

TABLE 1

Oligonucleotide primers and probe specific for sequences of the *M. tuberculosis* IS6110 gene

| SEQ ID NO | Oligonucleotide sequences (5'-3') | Length (mer) | Tm (° C.) |
|---|---|---|---|
| Outer Primers | | | |
| 2 | CACGTAGGCGAACCCTGCCCAGGTC | 25 | 66~76 |
| 3 | GCGTAGGCGTCGGTCACAAA | 20 | 64 |
| 4 | GTGAGGGCATCGAGGTGGCCAGATG | 25 | 64~76 |
| 5 | CGTGAGGGCATCGAGGTGGC | 20 | 68 |
| Inner Primers | | | |
| 6 | GACACATAGGTGAGGTCTGC | 20 | 46~55 |
| 7 | GCCACGTAGGCGAACCCTG | 19 | 64 |
| 8 | ACGGCTGATGACCAAACT | 18 | 47~56 |
| 9 | AGATGCACCGTCGAACGG | 18 | 58 |
| Probe | | | |
| 10 | TTTTTTTTTTACCTAACCGGCTGTGGGTAGCAGA | 34 | |

Example 2

Determining the Tm for Primers (a). Determination of Tm for outer primer pair SEQ ID NOS. 2 and 4.

1. Ingredient of reactants:

| | |
|---|---|
| DNA template | 1 μl |
| 10x buffer | 5 μl |
| OTNP001 | 5 μl |
| OTNP002 | 5 μl |
| dNTP | 1 μl |
| Taq | 0.4 μl |
| ddH$_2$O | 32.6 μl |
| Total | 50 μl |

The concentration of OTNP001 and OTNP002 is 10 μM.

2. Reaction condition:

```
94° C.,        5 minutes
    ↓
( 94° C.,       30 seconds )
( 63.9~80.5° C., 15 seconds )  30 Cycles
( 72° C.,       15 seconds )
    ↓
72° C.,        10 minutes
    ↓
4° C. for storage.
```

Figure 2:
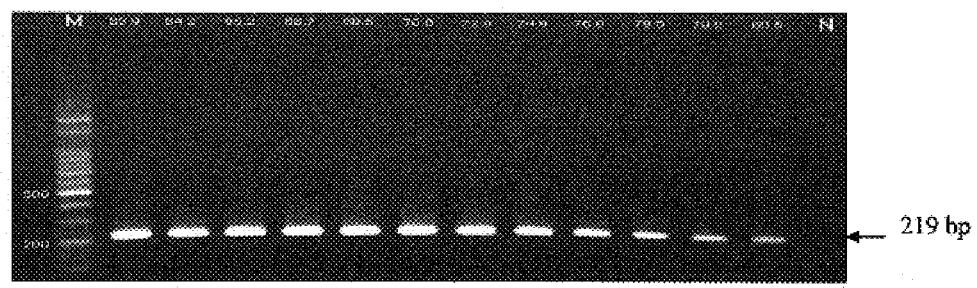
FIG. 2 shows (a) the determination of Tm for outer primer pair SEQ ID NOS. 2 and 4; and (b) the determination of Tm for outer primer pair SEQ ID Nos. 6 and 8. In this FIG. 2(*a*), "219 bp" means the 1$^{st}$ phase PCR product that amplified from IS6110 gene using as the target template for 2$^{nd}$ phase PCR (Inner primers' amplification). In this FIG. 2(*b*), "162 bp" means the 2$^{nd}$ phase PCR product amplified from 1$^{st}$ phase PCR using as the target for proof-reading by specific probe.
Figure 2:

The result was illustrated in FIG. 2(a).

(b). Determination of Tm for outer primer pair SEQ ID NOS. 6 and 8.

1. Ingredient of reactants:

| | |
|---|---|
| DNA template | 1 μl |
| 10x buffer | 5 μl |
| OTNP003 | 5 μl |
| OTNP004 | 5 μl |
| dNTP | 1 μl |
| Taq | 0.4 μl |
| ddH$_2$O | 32.6 μl |
| Total | 50 μl |

The concentration of OTNP003 and OTNP004 is 10 μM.

2. Reaction condition:

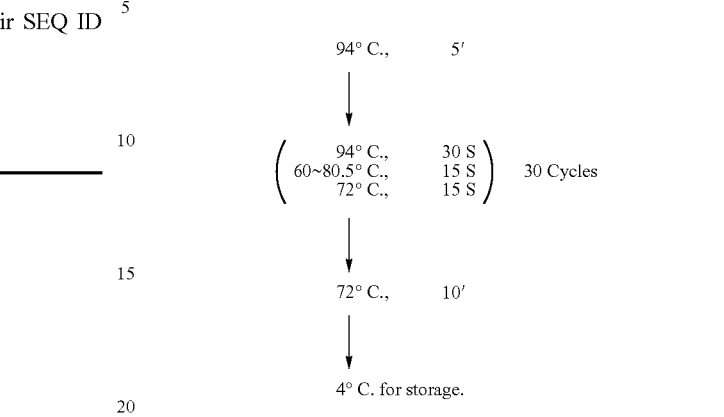

The result was illustrated in FIG. 2(b).

Example 3

Determining the Concentration of Primers

1. Ingredient of reactants:

| | |
|---|---|
| DNA template | 1 μl |
| 10x buffer | 5 μl |
| OTNP001 | 5 μl (0.05 μM) |
| OTNP002 | 5 μl (0.05 μM) |
| OTNP003 | 5 μl (1 or 2 μM) |
| OTNP004 | 5 μl (1 or 2 μM) |
| dNTP | 1.5 μl |
| Taq | 0.5 μl |
| ddH$_2$O | 22 μl |
| Total | 50 μl |

2. Reaction condition

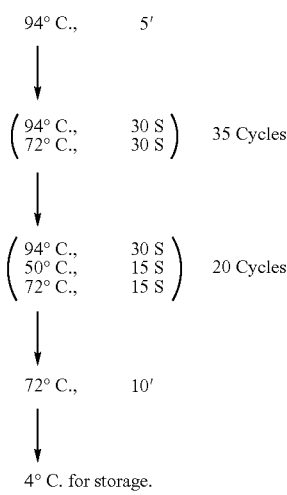

The result was illustrated in FIG. 3.

Example 4

Collecting Clinical Samples

I. Materials

Major Kit I:

(1) Lysis Buffer I (5 ml)

(2) Lysis Buffer II (4 ml)

(3) Hybridization Buffer (5 ml)

(4) Wash Buffer (60 ml)

(5) Lysis tubes (1.8 ml, 25 tubes)

(6) Hybridization tubes (12×75 mm, 50 tubes)

(7) Extension buffer (3 ml, stored in −20° C. after arriving)

II. Decontamination of Clinical Samples (Performed in P3 Level Laboratory by Each Medical Center)

(1) Clinical samples were collected and kept in 4° C. refrigerator.

(2) 1 g of NALC was dissolved into 100 ml of sterile 4% NaOH and 100 ml of 2.94% sodium citrate solution (Daily prepared).

(3) Equal volume of NaOH-citrate-NALC was added into each clinical sample.

(4) Sample tubes were vortexed for 30 second and inverted several times. Tubes were Kept in room temperature (RT) for 15 minutes.

(5) PBS was added to 50 ml level of sample tube, then centrifuged at 3000 rpm for 20 minutes.

(6) Supernatant was removed and 1 ml of PBS was used to resuspend precipitate.

III. Lysis of Precipitate (Can be Performed in P2 Laboratory)

(1) 10 ml ddH$_2$O was mixed with 1 ml of resuspended precipitate. Samples were vortexed for 20 sec, then centrifuged at 3,800 rpm for 15 min.

(2) Supernatant was removed; and 150 μl of Lysis buffer I was added and tubes were vortexed for 1 min. Tubes were kept at RT for 10 min.

(3). Lysis tubes were kept in 100° C. water bath for 20 min and then 125 μl of Lysis buffer II was added.

(4) Samples were centrifuged at 10,000 rpm for 2 min, DNA lysate was collected and stored in −20° C. freezer.

Example 5

One Tube Nested PCR

I. Set Up a New 0.2 ml Microfuge Tube by Adding up the Following Reagent:

| | |
|---|---|
| Sample | 1 λ |
| 10x buffer | 5 λ |
| Primer SEQ ID: NO. 2 | 5 λ* |
| Primer SEQ ID: NO. 4 | 5 λ* |
| Biotin-Primer SEQ ID: NO. 6 | 5 λ** |
| Primer SEQ ID: NO. 8 | 5 λ** |
| dNTP | 1.5 λ |

-continued

| | |
|---|---|
| Taq | 0.5 λ |
| ddH$_2$O | 22 λ |
| Total | 50 λ |

*The total concentration of primer SEQ ID: NOS. 2 and 4 is 0.1 μM.
**The total concentration of biotinylated primer SEQ ID: NO. 6 and primer SEQ ID: NO. 8 is 2.0 μM.

II. Initiate the Following Program With Heated Lid Enabled:

TABLE 2

The protocol of one tube nested PCR.

| | Temperature | Time | Number of cycles |
|---|---|---|---|
| 1 | 94° C. | 5 min | 1 |
| 2 | 94° C. | 30 sec | 35 |
|  | 72° C. | 30 sec |  |
| 3 | 94° C. | 30 sec | 20 |
|  | 50° C. | 15 sec |  |
|  | 72° C. | 15 sec |  |
| 4 | 72° C. | 10 min | 1 |
| 5 | 4° C. | Hold | — |

Example 6

Detection of Amplification Product

I. Materials

Detection kit-I: (219 reactions/kit, store in 4° C.)

(1) Blocking buffer (0.5%, 60 ml, stored in 4° C.)

(2) Substrate A (7.5 ml, stored in 4° C.) (PIERCE, prod# 37075)

(3) Substrate B (7.5 ml, stored in 4° C.) (PIERCE, prod# 37075)

Detection kit-II: (219 reactions/kit, store in −20° C.)

(1) Bioactive catalyst (BC,PIERCE, prod# 21127; 1 mg/ml, 15 μl, stored in −20° C.)

Other Material and Equipments:

(1) Magnetic Rack (2) NALC (N-acetyl-L-cysteine)

(3) 4% NaOH solution (4) 2.94% sodium citrate solution (5) PBS, pH7.0

(6) 0.1% PBST (PBS with 0.1% tween-20)

(7) 0.5% PBST (PBS with 0.5% tween-20)

(8) Magnetic Dry Bath (9) Berthol Luminometer with PC connection

II. Procedures (1) 200 μl of blocking solution was added into each tube. The tube was vortexed to separate magnetic beads.

(2) 5 μl of freshly prepared bioactive catalyst (BC, one side could combine with biotin and the other side could react with substrate B) solution was added. Each tube was vortexed and dispersed evenly. Tubes were let sit at room temperature for 20 min.

(3) Hybridization tubes were moved into magnetic rack and sit for 5 min. Then solution was removed by aspiration. Magnetic beads could not be interfered.

(4) 1 ml of 0.5% PBST was added. Tubes were vortexed to separate magnetic beads and put tubes back to magnetic rack. After 5 minutes, then solution was removed by aspiration. The step was repeated once.

(5) 200 µl of PBS was added in each tube to re-suspend magnetic beads by vortexing.

(6) 20 µl of solution with re-suspended magnetic beads was added to a new hybridization tube.

(7) 50 µl of mixed substrate (25 µl substrate A plus 25 µl substrate B) was added to each tube.

(8) Luminescence of samples was automatically measured by Luminometer.

III. Interpretation of Results

The control group ddH$_2$O was tested prior to testing on samples. If the value per 10 seconds was read as equal to or greater than 25,000 RLU, this test should be re-tested. If the value per 10 seconds was read as smaller than 25,000 RLU, the test results on the samples should be interpreted as follows:

(1) In case of equal to or greater than 100,000 RLU, the result is regarded as positive for *M. tuberculosis* complex;

(2) In case of smaller than 25,000 RLU, the result is regarded as negative for *M. tuberculosis* complex; and (3) In case of 25,000~100,000 RLU, the result is regarded as probable for *M. tuberculosis* complex. This test should be re-tested and the result should be interpreted as follows:

(a) Retest value ≧25,000 RLU: Positive for *M. tuberculosis* complex.

(b) Retest value <25,000 RLU: Negative for *M. tuberculosis* complex.

Example 7

Following the above procedures, clinical samples of NC, NIM, MAC, MAC, PC, TB tissue from patients and controls were assayed with the method of the present invention (FIG. 4). The results clearly agreed to the result of the MTB assay of the invention (FIG. 5), a two-tube nested PCR method that was previously disclosed. The method of the present invention, while maintaining the same accuracy as the MTB assay of the invention (FIG. 6), has the advantage of performing the nested PCR in one tube, thereby reducing chances of contamination.

Example 8

Clinical samples, both positive and negative cases determined by culture confirmation (the gold standard), one tube and two-tube nested PCR, were examined by the invention. The results in FIG. 6 showed that the one tube nested PCR method of the invention achieved extremely high sensitivity and specificity.

While the invention has been described and exemplified in sufficient detail for those skilled in this art to produce and use it, various alternatives, modifications, and improvements should be apparent without departing from the spirit. and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A kit for detecting the presence or absence of *Mycobacterium tuberculosis* in a sample using a nested polymerase chain reaction, comprising
    (I) an outer pair of oligonucleotide primers selected from the group consisting of (a) SEQ ID NOS: 2 and 4, and (b) SEQ ID NOS: 3 and 5, and
    (ii) an inner pair of oligonucleotide primers selected from the group consisting of (c) SEQ ID NOS: 6 and 8, and (d) SEQ ID NOS: 7 and 9.

2. The kit of claim 1, wherein the outer pair of oligonucleotide primers is SEQ ID NOS: 2 and 4, and the inner pair of oligonucleotide primers is SEQ ID NOS: 6 and 8.

3. The kit of claim 1, wherein the inner pair of oligonucleotide primers is labeled by a detectable group selected from the group consisting of fluorescent molecules, radioactive molecules, chromogenic substrates, biotin, acridinium ester and acridinium-9-carboxamide.

4. The kit of claim 1, which further comprises a probe wherein the sequence of the probe is SEQ ID NO. 10.

5. A method for detecting the presence or absence of *Mycobacterium tuberculosis* in a sample using a nested polymerase chain reaction, comprising
    (I) adding into one tube with DNA from the sample, buffer, dNTP, Taq polymerase, probe having SEQ ID NO: 10, an outer pair of oligonucleotide primers selected from the group consisting of (a) SEQ ID NOS: 2 and 4, and (b) SEQ ID NOS: 3 and 5, and an inner pair of oligonucleotide primers selected from the group consisting of (c) SEQ ID NOS: 6 and 8, and (d) SEQ ID NOS: 7 and 9 to form a mixture, wherein the concentration of the outer pair of oligonucleotide primers to the concentration of the inner pair of oligonucleotide primers is 1:5 o 1:100;
    (ii) performing first 20-50 cycles of amplification for PCR products from the outer primers in the first-stage polymerase chain reaction;
    (iii) performing following 10-30 cycles of amplification PCR products from for the inner primers in the second-stage polymerase chain reaction; and
    (iv) identifying *M. tuberculosis* by the probe.

6. The method of claim 5, wherein the temperature of annealing and the temperature of extension in the first-stage polymerase chain reaction is at 72° C.

7. The method of claim 5, which further comprises treating the mixture of step (I) over 5 minutes at 94° C.

8. The method of claim 5, wherein the outer pair of oligonucleotide primers is SEQ ID NOS: 2 and 4, and the inner pair of oligonucleotide primers is SEQ ID NOS: 6 and 8.

9. The method of claim 5, wherein the concentration of the outer pair of oligonucleotide primers to inner pair of oligonucleotide primers is 1:10 to 1:50.

10. The method of claim 9, wherein the concentration of the outer pair of oligonucleotide primers to inner pair of oligonucleotide primers is 1:20.

11. The method of claim 5, wherein the cycle of amplification for PCR products from the outer primers is 25-45.

12. The method of claim 11, wherein the cycle of amplification for PCR products from the outer primers in the first polymerase chain reaction is 35.

13. The method of claim 5, wherein the cycle of amplification for PCR products from the inner primers is 10-30.

14. The method of claim 13, wherein the cycle of amplification for PCR products from the inner primers is 20.

15. The method of claim 5, wherein the inner pair of oligonucleotide primers is labeled by a detectable group selected from the group consisting of fluorescent molecules, radioactive molecules, chromogenic substrates, biotin, acridinium ester and acridinium-9-carboxamide.

16. The method of claim 5, wherein the probe is SEQ ID No. 10.

17. The method of claim 5, wherein the nested PCR reaction is performed in one tube.

* * * * *